United States Patent [19]

Tracy

[11] Patent Number: 5,797,824
[45] Date of Patent: *Aug. 25, 1998

[54] DISPOSABLE DIAPER WITH PADDED WAISTBAND AND LEGHOLES

[76] Inventor: Rhonda Tracy, 233 Grandview, Glen Ellyn, Ill. 6013

[*] Notice: The term of this patent shall not extend beyond the expiration date of Pat. No. 5,064,421.7

[21] Appl. No.: 92,540

[22] Filed: Jul. 16, 1993

Related U.S. Application Data

[63] Continuation of Ser. No. 790,469, Nov. 12, 1991, abandoned, which is a continuation of Ser. No. 516,473, Apr. 30, 1990, Pat. No. 5,064,421, which is a continuation of Ser. No. 93,681, Sep. 8, 1987, abandoned.

[51] Int. Cl.⁶ .................................................. A61F 13/15
[52] U.S. Cl. ................ 604/385.1; 604/386; 604/389; 604/369
[58] Field of Search ......................... 604/358, 369, 604/385.1, 385.2, 378, 389

[56] References Cited

U.S. PATENT DOCUMENTS

| | | | |
|---|---|---|---|
| 1,329,119 | 1/1920 | George. | |
| 2,649,858 | 8/1953 | Le Bolt | 604/378 |
| 3,237,625 | 3/1966 | Johnson | 604/378 |
| 3,461,872 | 8/1969 | McConnell et al. | 604/369 |
| 3,568,676 | 3/1971 | Del Guerco | 604/378 |
| 3,612,055 | 10/1971 | Mesek et al. | |
| 3,842,837 | 10/1974 | Sward. | |
| 3,882,870 | 5/1975 | Hathoway. | |
| 4,102,340 | 7/1978 | Mesek et al. | |
| 4,230,113 | 10/1980 | Mehta. | |
| 4,670,011 | 6/1987 | Mesek. | |
| 4,728,326 | 3/1988 | Gilles | 604/391 |
| 4,743,239 | 5/1988 | Cole. | |
| 4,753,645 | 6/1988 | Johnson. | |
| 4,978,570 | 12/1990 | Heyn et al. | 604/369 |
| 5,064,421 | 11/1991 | Tracy | 604/385.1 |
| 5,207,662 | 5/1993 | James | 604/385.2 |

FOREIGN PATENT DOCUMENTS 2174591 11/1986 United Kingdom .................. 604/358

*Primary Examiner*—Robert A. Clarke
*Attorney, Agent, or Firm*—Edward D. Manzo

[57] ABSTRACT

A disposable diaper having a front section, rear section, crotch portion, and a waist band. A soft padding is provided on the waist band. Padding is also provided on the edge portions surrounding the leg holes.

15 Claims, 1 Drawing Sheet

DISPOSABLE DIAPER WITH PADDED WAISTBAND AND LEGHOLES

This is a continuation of my application Ser. No. 790,469 filed Nov. 12, 1991, now abandoned which is a continuation of Ser. No. 516,473 filed Apr. 30, 1990, now U.S. Pat. No. 5,064,421, which is a continuation of application Ser. No. 093,681, Sep. 8, 1987, now abandoned.

BACKGROUND OF THE INVENTION

1. Field of the Invention

This invention relates in general to a disposable diaper and more specifically, to a disposable diaper having a padded waistband and legholes.

2. Description of the Prior Art

Disposable diapers have largely replaced the common cloth diaper to be worn by infants and toddlers. Disposable diapers not only can be easily discarded, but are adjustable and convenient to attach and remove. Known diapers of the disposable variety are typically capable of effective retention of liquid and solid material without having to resort to protective covers as was required by cloth diapers. Although known disposable diaper designs are generally satisfactory, several problems haven arisen in their use. The waist band and border around the legholes of prior art disposable diapers are commonly an unprotected plastic band and the like. Such bands are uncomfortable when worn and often such material is stiff, and scratches and abrades an infant's skin. In addition, known waist bands and leg bands in disposable diapers do not provide an optimum barrier against leakage and seepage, which is so desirable.

SUMMARY OF THE INVENTION

It is therefore an objective of the invention to provide a disposable diaper having padded waist and leg areas. The padding as herein disclosed covers the the plastic waistline band from inside to outside of the diaper when worn by the baby. The padding may be in the form of strips of soft pliable material, such as cotton and the like, and extends substantially around the waist. The soft padding protects the infant and toddler from scratches, irritations, and abrasions commonly inflicted by known diaper designs. The strip of padding further performs the added function of inhibiting leakage from within the diaper. The protection provided by the padding not only exists within the waist line portion of the diaper, but is also present at the top and outside of the diaper where the skin may overlap when worn.

The disposable diaper herein disclosed further includes strips of soft material, such as cotton and the like, at the edge portions of the diaper that surrond the legs of the wearer to accomplish similar functions as the padding at the waist areas.

DESCRIPTION OF THE PREFERRED EMBODIMENT

Figure 1:
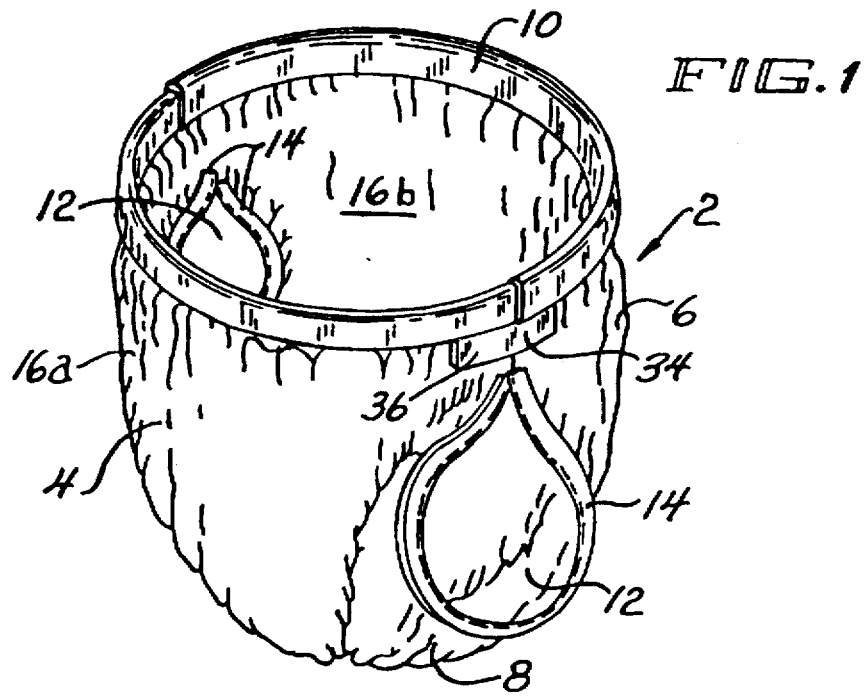
FIG. 1 is a perspective view, with parts of the wasitline padding removed, of the disposable diaper of the invention.

Referring now to FIGS. 1–4, there is illustrated the disposable diaper with padded waistline and legholes of the invention, generally designated by reference numeral 2. In its closed configuration as it is worn in the form of FIG. 1, the diaper 2 is formed with a typical front section 4, a back section 6, a crotch area 8, and a top portion 10 forming an adjustable waistline construction. Leg holes 12 are defined by edge portions 14 of disposable diaper 2. The diaper 2 is formed in multiple superimposed sheets of material in front section 4, back section 6 and crotch area 8, including an outer liquid impervious outer sheet 16a and an inner liquid permeable sheet 16b as is well known. One or more layers 18 (FIGS. 3 and 4) of a liquid absorbent material, such as cotton, pulp and the like, is imposed between the outer sheet 16a and the inner sheet 16b as is conventional. The thickness of inner material 18 may be thickened in the crotch area 8 and elsewhere for greater liquid absorption.

Figure 2:
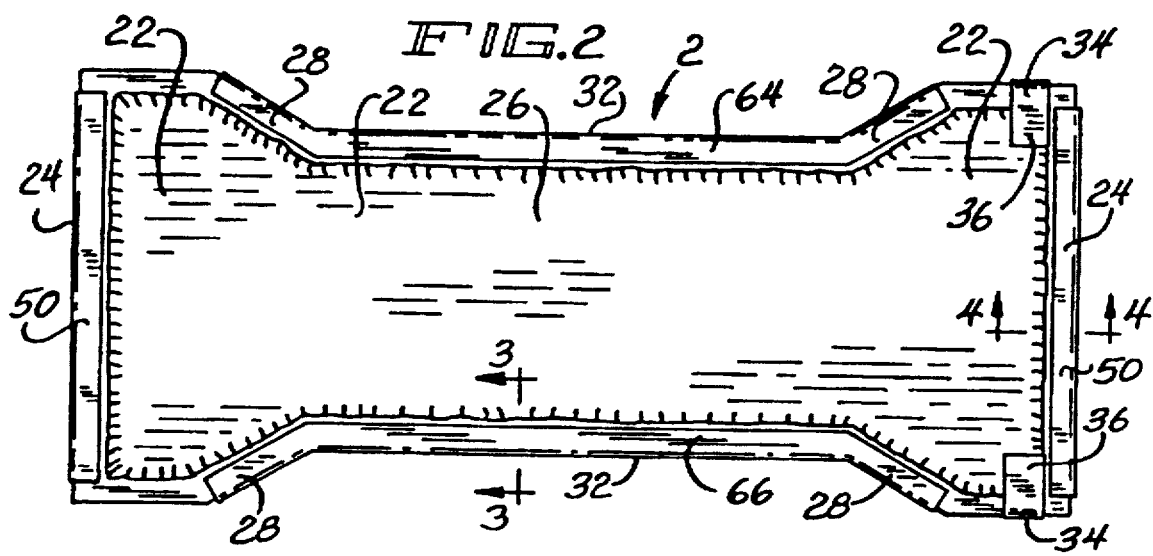
FIG. 2 is a rear plan view showing the inside of the diaper of FIG. 1 in a flat configuration.
Figure 3:
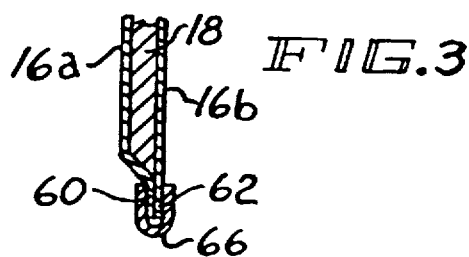
FIG. 3 is a partial end view, with parts in section, showing the portion of the diaper forming the legholes in the configuration of FIG. 1.
Figure 3:

The diaper 2 in its flat configuration as shown in FIG. 2 is formed as a single body 20 having enlarged end portions 22 which terminate at edges 24 that form the top waist band portion 10 shown in FIG. 1. The intermediate section 26 of body 20 includes tapered edges 28 and a central section having opposed edges 32 that form the edge potions 14 of the leg holes 12. A pair of plastic adhesive strips 34 and the like having a detachable free end 36 are affixed on one enlarged end portion 22 of the body 20 to permit the diaper 2 to be adjustably affixed to the opposite end portion 22 to secure the diaper to the infant as in the configuration shown in FIG. 1.

Figure 4:
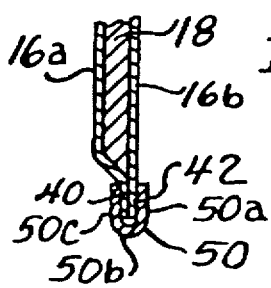
FIG. 4 is an end view, with parts in section, showing the edge portions of the diaper forming the waist band areas.
Figure 4:

Referring now to FIGS. 1, 2, and 4, the waistline portion 10 is formed by border sections 40, 42 of the inner and outer sheets 16a and 16b which are affixed together. The border sections 40, 42 are fabricated from a plastic material or similar material. A outer strip 50 of soft material in the form of a strip of cotton or other non-abrasive material is bent lengthwise over the border sections 40, 42 of a plastic material and the like located on each of the enlarged sections 22 in FIG. 2 in affixed relationship by an suitable technique of attachment. The strip 50 forms surfaces 50a, 50b, and 50c that are respectively positioned from inside to outside of the diaper 2 so as to provide a soft cushion or pad substantially over the exposed surfaces of border sections 40, 42 to protect the skin of the infant or toddler and provide an additional absorbent barrier to alleviate leakage. The strip 50 may be formed as a pair of strips to generally extend 360 degrees at the waist in the configuration of FIG. 1 (one of the strips 50 being cut away in FIG. 1 for illustrative purposes).

Referring again to FIGS. 1, 2, and 4, the edge portions 12 for leg holes 14 are similarly constructed as the waist band as previously described. The plastic borders 60, 62 are affixed together (FIG. 3) and are covered in affixed relationship by strips 64, 66 of a soft material, such as cotton, to cover the exposed surfaces of borders 60, 62 to serve the same function at leg holes 14 as soft strips 50 at the waist band.

What is claimed is:

1. A disposable diaper comprising:
   a body portion having two enlarged end portions and a narrowed intermediate portion therebetween, the body portion being shaped so that said diaper may extend about a waist and crotch of a wearer and have an inside and an outside with respect to the wearer;

each end portion having a respective waistband portion at an edge thereof so that when the diaper is worn, the waistband portions gird the waist of the wearer;

at least two body-portion layers including a layer of liquid-absorbent material and a plastic layer having an edge at the edge of the diaper;

a soft padding member located along at least one of said waistband portions, being adjacent to said plastic layer edge, the soft padding member being distinct from all of said body-portion layer, the soft padding member including a material formed from a soft substance presenting a soft surface along at least a portion of said inside of the diaper waistband portion despite said plastic layer edge.

2. The diaper according to claim 1 wherein said padding member comprises a first strip of soft padding parallel to the waistband, the first strip providing an additional absorbent barrier against leakage.

3. The diaper of claim 2 wherein said first strip wraps around from the inside to the outside of the waistband.

4. The diaper of claim 3 wherein said diaper includes an inside sheet and an outside sheet, said liquid-absorbent material being located between said sheets; wherein said sheets terminate longitudinally at said waistband; and wherein said first strip wraps around said inside and outside sheets.

5. The diaper of claim 4 further comprising second and third strips of soft padding material, distinct from said liquid-absorbent material, located along leg hole portions of said diaper, each of said second and third strips wrapping around lateral edges of inside and outside sheets.

6. The diaper according to claim 1 wherein said intermediate portion forms leg holes when said diaper is worn, and wherein the diaper further comprises:

further soft padding members, distinct from said layer of liquid-absorbent material, said further soft padding members being located along said leg holes to provide a soft surface at said leg holes.

7. The diaper of claim 6 wherein said further padding members comprise second and third strips located along respective edges of said intermediate portion.

8. The diaper of claim 7 wherein each of said second and third strips wraps around from the inside to the outside of its corresponding intermediate portion edge.

9. The diaper of claim 1 wherein said soft padding member is adjacent to and does not overlap said layer of liquid-absorbent material.

10. A disposable diaper to be worn by a wearer comprising:

a multi-ply body portion having two enlarged end portions and a narrowed intermediate portion therebetween;

attachment devices affixed to said end portions so that said diaper may be closed about a waist and crotch of a wearer and have an inside and an outside with respect to the wearer;

each end portion having a respective waistband portion at an edge thereof so that when the diaper is worn, the waistband portions gird the waist of the wearer;

the body portion having an inside ply, an outside ply, and a layer of liquid-absorbent material therebetween, said inside ply and said outside ply extending beyond said layer of liquid-absorbing material at edges of said diaper, at least one of said plies including a plastic material extending to an edge of the body portion;

a first soft padding member, distinct from said layer of liquid absorbent material and said plies, the first soft padding member including a strip of a soft substance located along at least one of said waistband portions, the soft padding member being located substantially only along the waistband at the inside of said diaper with respect to the wearer thereby to present a soft surface at said inside of the diaper waistband despite the plastic material at the edge of the body portion.

11. The diaper of claim 10 further comprising second and third soft padding members distinct from said layer of liquid-absorbent material, each of said second and third soft padding members being located substantially only at corresponding leg hole edges of the body portion.

12. The diaper of claim 11 wherein said first, second, and third soft padding members comprise strips that are external to said inside ply and said outside ply at said edges of the diaper.

13. The diaper of claim 11 wherein each of said first, second and third soft padding members is adjacent to but does not overlap said layer of liquid-absorbent material.

14. The diaper of claim 10 wherein said soft padding member is adjacent to and does not overlap said layer of liquid-absorbent material.

15. A disposable diaper comprising:

a body portion having a single piece with two enlarged opposed end portions and a narrowed intermediate portion disposed between said opposed end portions, the body portion being arranged to be worn by an individual, said opposed end portions each having an opposite edge portion;

the body portion having a layer of liquid absorbent material;

the diaper including a waist band portion on opposite edge portions of the opposed enlarged end portions;

the waist band including plastic material at border edges thereof;

attachment devices affixed to one of the opposed end portions having members to be affixed to the other one of the opposed end portions, the waist band forming a substantially continuous waistband to extend generally around the waist of the individual;

the waist band including a padding member extending along an opposite edge portion at an exposed surface of the waist band;

the padding member including at least one strip of material formed from a soft substance;

the at least one strip of material forming a soft surface for contact with the skin of the individual at at least one of the border edges.

* * * * *